(12) United States Patent
Arless et al.

(10) Patent No.: US 8,945,106 B2
(45) Date of Patent: Feb. 3, 2015

(54) TIP DESIGN FOR CRYOGENIC PROBE WITH INNER COIL INJECTION TUBE

(76) Inventors: Steve Arless, Montreal (CA); Daniel Nahon, Ottawa (CA); Domenic Santoianni, Kirkland (CA)

(*) Notice: Subject to any disclaimer, the term of this patent is extended or adjusted under 35 U.S.C. 154(b) by 1002 days.

(21) Appl. No.: 12/496,887

(22) Filed: Jul. 2, 2009

(65) Prior Publication Data

US 2010/0057063 A1 Mar. 4, 2010

Related U.S. Application Data

(60) Provisional application No. 61/078,216, filed on Jul. 3, 2008.

(51) Int. Cl.
*A61B 18/02* (2006.01)

(52) U.S. Cl.
CPC .......... *A61B 18/02* (2013.01); *A61B 2018/0212* (2013.01); *A61B 2018/0262* (2013.01)
USPC .............. 606/21; 606/20; 606/22; 606/23

(58) Field of Classification Search
USPC .............. 606/21–23, 25, 26, 41; 128/898; 604/113
See application file for complete search history.

(56) References Cited

U.S. PATENT DOCUMENTS

| | | | |
|---|---|---|---|
| 3,228,400 A * | 1/1966 | Armao | 606/21 |
| 3,971,383 A | 7/1976 | Van Gerven | |
| 4,377,168 A | 3/1983 | Rzasa et al. | |
| 4,831,846 A | 5/1989 | Sungaila | |
| 5,520,682 A | 5/1996 | Baust et al. | |
| 5,735,847 A * | 4/1998 | Gough et al. | 606/41 |
| 5,899,898 A | 5/1999 | Arless et al. | |
| 5,899,899 A | 5/1999 | Arless et al. | |
| 6,106,518 A * | 8/2000 | Wittenberger et al. | 606/21 |
| 6,171,301 B1 | 1/2001 | Nelson et al. | |
| 6,235,048 B1 * | 5/2001 | Dobak, III | 606/23 |
| 6,488,659 B1 * | 12/2002 | Rosenman | 604/113 |
| 6,508,814 B2 | 1/2003 | Tortal et al. | |
| 6,547,784 B1 | 4/2003 | Thompson et al. | |
| 6,551,309 B1 | 4/2003 | Le Pivert | |
| 6,648,879 B2 | 11/2003 | Joye et al. | |
| 6,875,209 B2 | 4/2005 | Zvuloni et al. | |
| 7,083,612 B2 | 8/2006 | Littrup et al. | |
| 7,156,840 B2 | 1/2007 | Lentz et al. | |
| 7,160,291 B2 | 1/2007 | Damasco et al. | |
| 7,163,535 B2 | 1/2007 | Ryba | |
| 7,207,985 B2 | 4/2007 | Duong et al. | |
| 7,303,554 B2 | 12/2007 | Lalonde et al. | |
| 7,306,590 B2 | 12/2007 | Swanson | |
| 7,404,816 B2 | 7/2008 | Abboud et al. | |
| 7,416,548 B2 | 8/2008 | Baust et al. | |

(Continued)

*Primary Examiner* — Michael Peffley
*Assistant Examiner* — Khadijeh Vahdat
(74) *Attorney, Agent, or Firm* — McDonnell Boehnen Hulbert & Berghoff LLP

(57) ABSTRACT

A cryogenic probe design is provided containing, for example, an inner coil injection tube with a continuous flow of circulating liquid and an outer jacket enclosing the inner coil injection tube. A transducer may monitor parameters in the region between the inner coil injection tube and the outer jacket. An outer jacket serves to prevent gas leakage. One or more embodiments of a probe design provide continuous flow for example via a continuous and controlled path from inlet to outlet and an expanded thermally transmissive region. Expanding a thermally transmissive region of the cooling zone may be provided, for example, in one or more embodiments of injection tube designs.

31 Claims, 21 Drawing Sheets

(56) References Cited

U.S. PATENT DOCUMENTS

| | | | |
|---|---|---|---|
| 7,527,622 B2* | 5/2009 | Lane et al. | 606/21 |
| 2001/0007951 A1* | 7/2001 | Dobak, III | 607/106 |
| 2002/0022832 A1* | 2/2002 | Mikus et al. | 606/20 |
| 2002/0045893 A1* | 4/2002 | Lane et al. | 606/21 |
| 2002/0062122 A1* | 5/2002 | Lehmann et al. | 606/23 |
| 2003/0088240 A1* | 5/2003 | Saadat | 606/21 |
| 2004/0044334 A1* | 3/2004 | LaFontaine | 606/21 |
| 2004/0215294 A1 | 10/2004 | Littrup et al. | |
| 2006/0079867 A1 | 4/2006 | Berzak et al. | |
| 2006/0129142 A1 | 6/2006 | Reynolds | |
| 2007/0021741 A1 | 1/2007 | Abboud et al. | |
| 2007/0043342 A1* | 2/2007 | Kleinberger | 606/21 |
| 2007/0233055 A1 | 10/2007 | Abboud et al. | |
| 2007/0244474 A1 | 10/2007 | DeLonzor et al. | |

* cited by examiner

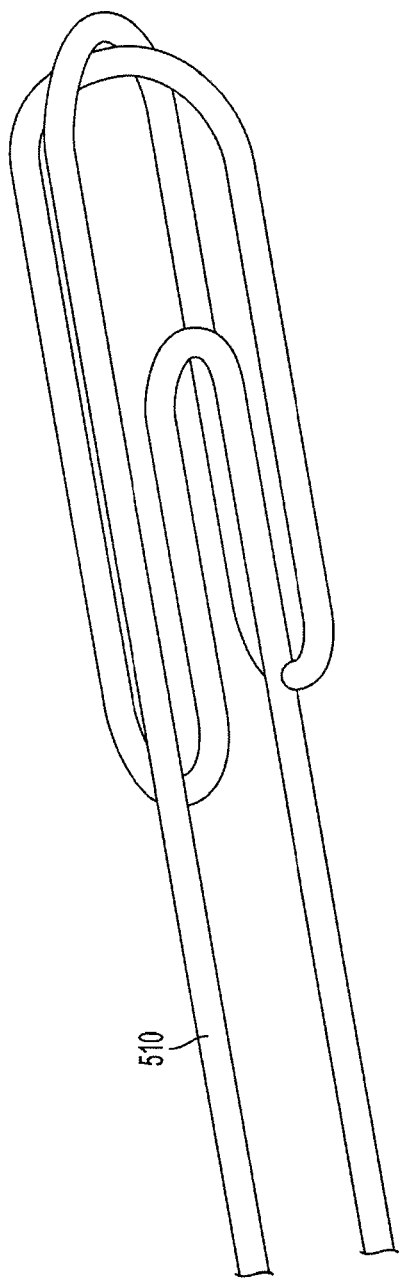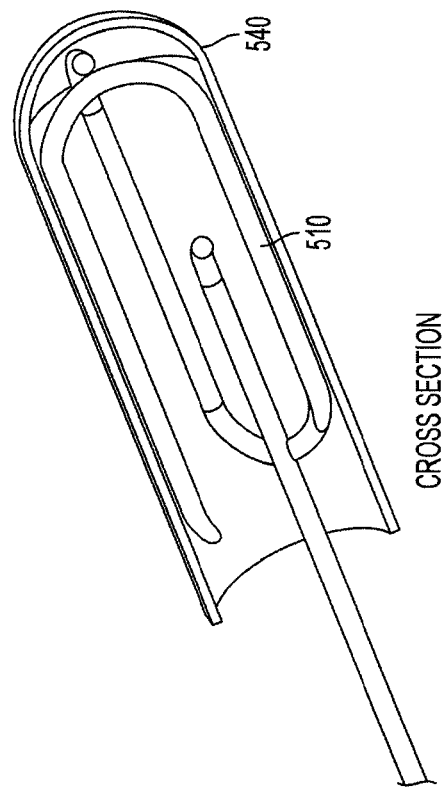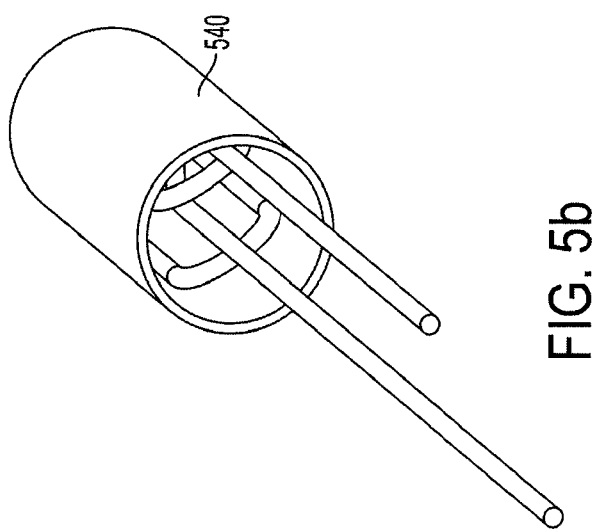
FIG. 5a
FIG. 5c CROSS SECTION
FIG. 5b

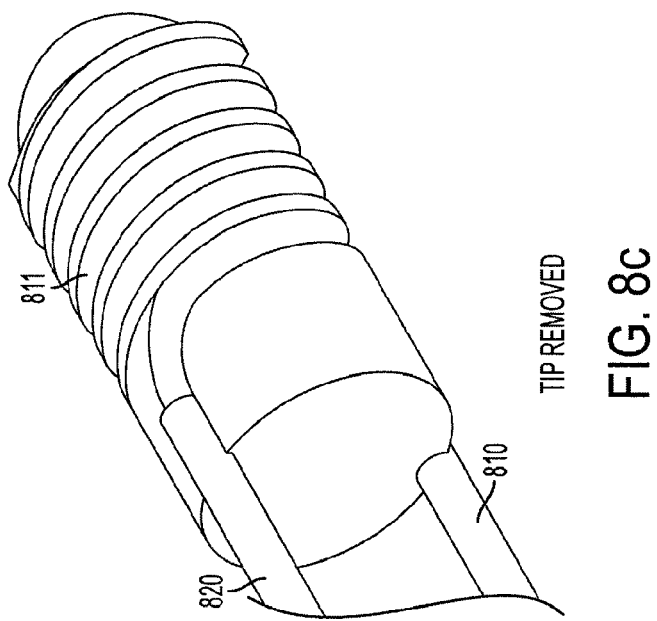
FIG. 8c TIP REMOVED
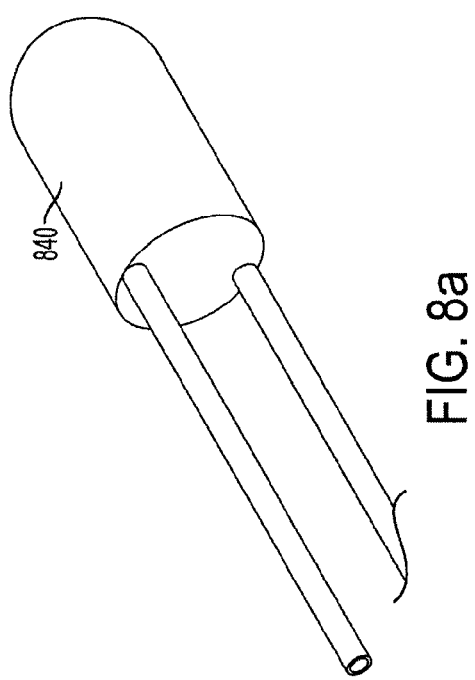
FIG. 8a
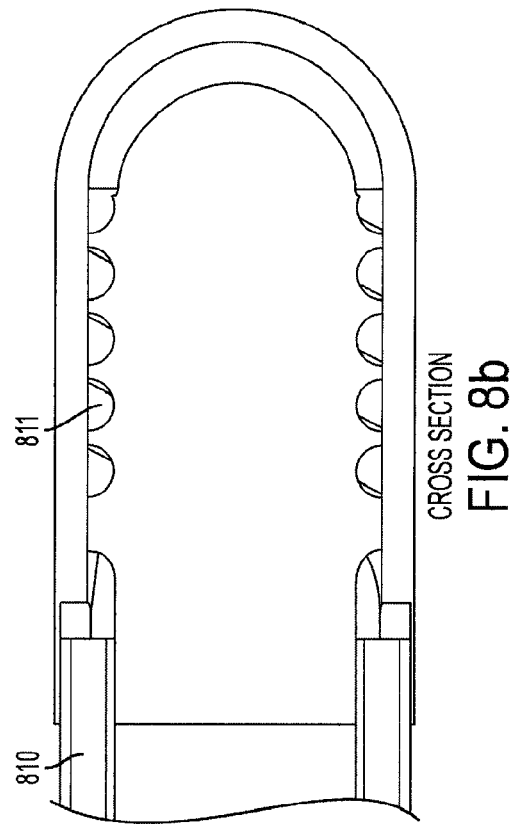
FIG. 8b CROSS SECTION

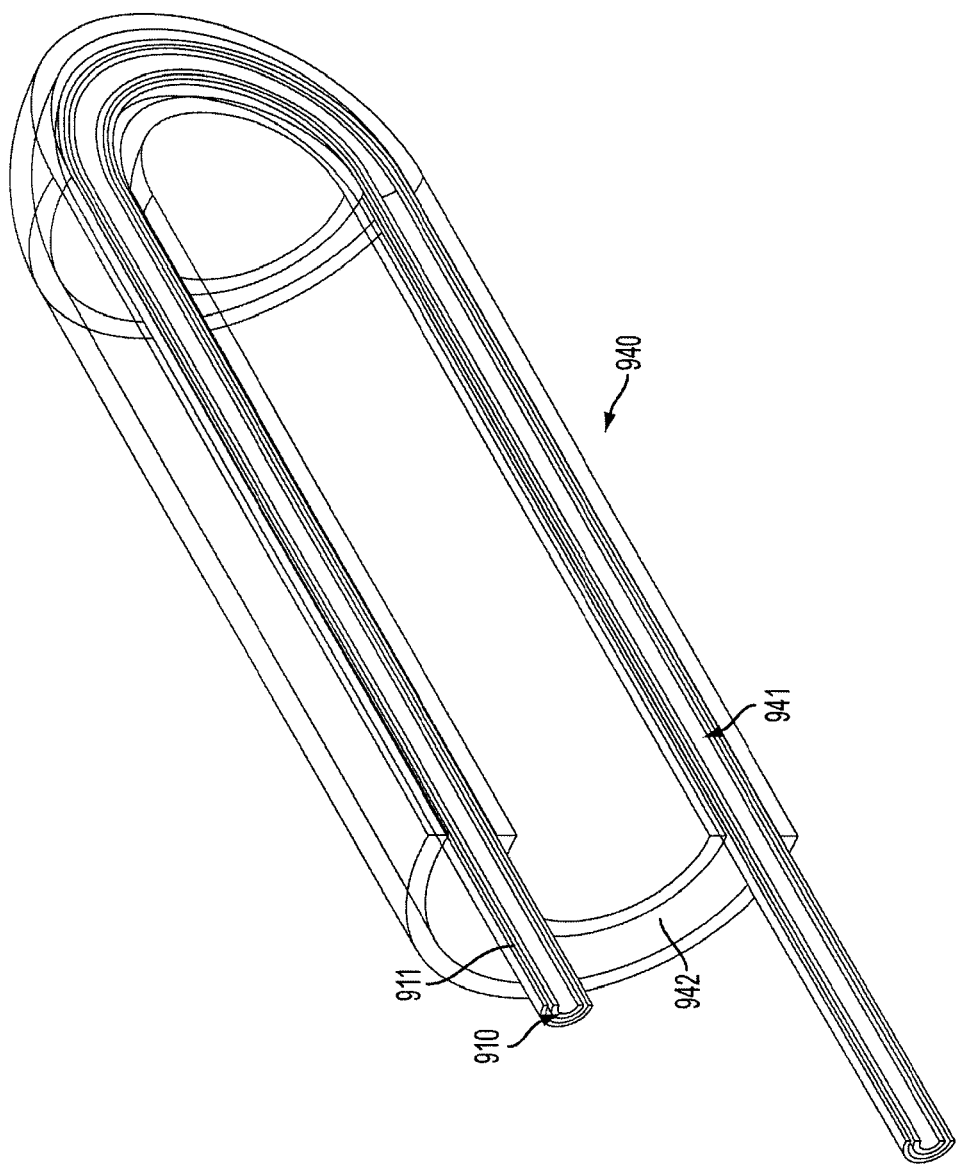

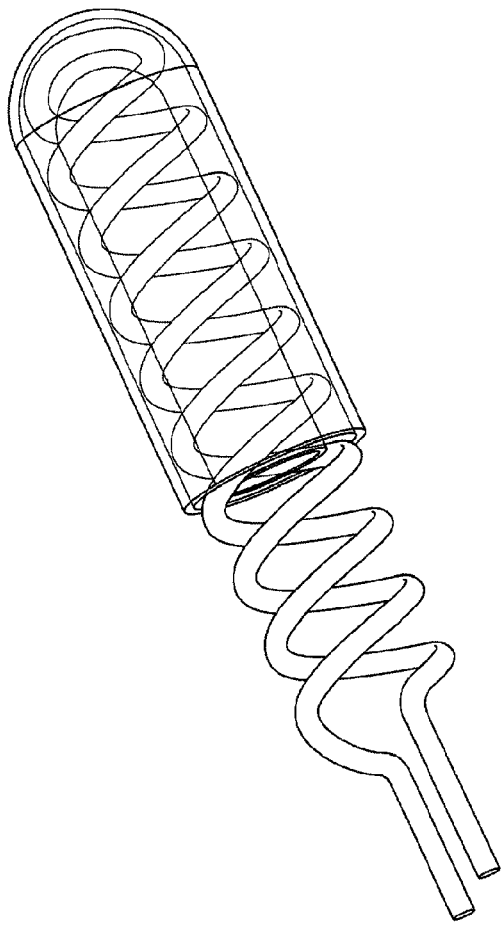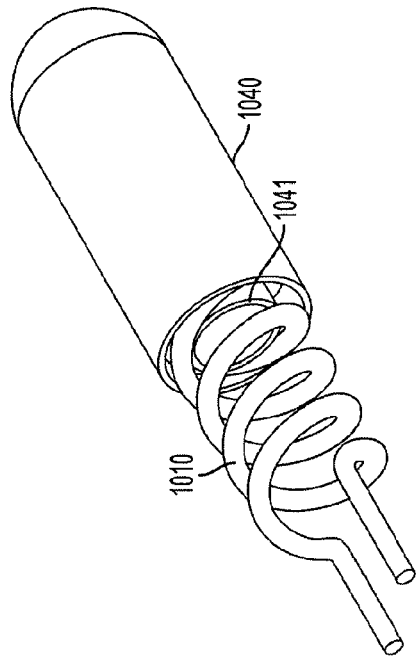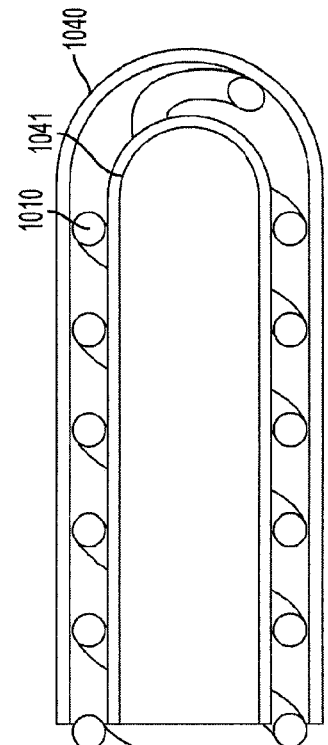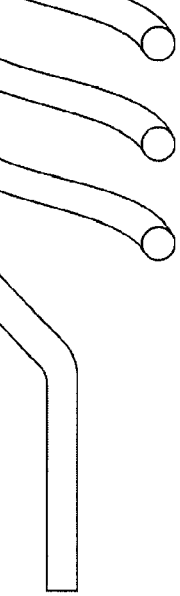
FIG. 10a
FIG. 10b
FIG. 10c
CROSS SECTION   NOTE: TUBE NOT SHOWN HOLLOW

TIP DESIGN FOR CRYOGENIC PROBE WITH INNER COIL INJECTION TUBE

RELATED APPLICATIONS

This application is related to and claims the benefit under 35 U.S.C. §119 of U.S. provisional patent application Ser. No. 61/078,216, entitled "Tip Design for Cryogenic Probe with Inner Coil Injection Tube," filed on Jul. 3, 2008, which is incorporated herein by reference in its entirety.

FIELD OF THE INVENTION

The field of this invention relates, for example, to a design for a cryogenic probe, and more specifically to various embodiments of cryogenic probes with, for example, one or more inner coil injection tubes and an outer jacket.

BACKGROUND

The use of cryogenic probes in surgical or percutaneous transcatheter applications has been in existence for quite some time. There are several designs of cryorefrigerant systems for medical applications: Joule Thomson (with or without phase change) ("JT") and circulating liquid ("CL") where cooling occurs through direct heat transfer without a Joule Thomson effect. For cardiovascular applications, designers may be concerned with maximizing cooling performance while at the same time detecting and/or preventing fluid egress from the probe since this may result in catastrophic gas emboli in the bloodstream.

In a JT system, the fluid (gas or liquid) flows though an injection line to the cooling tip and undergoes a rapid pressure drop, and potentially a phase change, expansion at the nozzle tip of the injection line. It is this expansion, called Joule Thomson effect, with or without phase change that is endothermic and creates cold in the surrounding region. A number of systems have been designed to detect and prevent gas egress in such cases: double balloons, tip pressure containment and tip pressure detection.

In a CL system, a refrigerant (usually liquid) flows though the injection line and returns through a return line. The tip is cooled through a direct heat exchange between the injection line and the inner surface of the tip. Unlike the JT system, the refrigerant does not undergo a Joule Thomson expansion inside the tip and cooling occurs through direct heat transfer. Early CL systems used saline or other materials that are liquid at atmospheric room temperature. New CL systems now under development, as in U.S. Pat. No. 7,083,612 to Littrup, are using high pressure fluids such as Nitrogen (so called Critical Nitrogen) or other compressed liquid gasses in the injection line. These new systems have the potential to be much more powerful but also carry the added risk for cardiovascular applications due to high pressures and associated leaks leading to gas emboli entering into the bloodstream.

Accordingly, a need exists for an improved system design for example, to an efficient heat transfer at the tip and to both monitor and contain a leak in the system.

SUMMARY OF THE INVENTION

One embodiment of the invention is provided, by example, with a cryogenic probe containing an inner coil injection tube with a continuous flow of circulating liquid and an outer jacket enclosing the inner coil injection tube. Also located within the outer jacket enclosure may be a temperature and/or a pressure transducer.

In another embodiment of the present invention, the cryogenic probe may contain an insulator or chamber that is enclosed by an outer jacket containing an inner coil injection tube. In this embodiment, the outer jacket may be designed or made of material, for example, that maintains relatively isotropic thermal and barometric conditions within the jacket and a temperature and/or pressure transducer may be located within the jacket. The outer jacket material may be polymeric, metallic or some combination thereof. The outside surface may be smooth or not depending on the mechanical characteristics desired for that particular application.

In another embodiment of the present invention, the cryogenic probe contains an insulator or chamber that is enclosed by an inner jacket with an inner coil injection tube partially embedded therein and an outer jacket enclosing the inner coil injection tube. In this embodiment a temperature and/or pressure transducer may be located within the jacket.

Certain alternative embodiments of the present invention include various alternative designs for end loops in various locations, densities, and amounts, in, for example, an inner coil element to improve upon flow and temperature transfer efficiencies, particularly for example near the tip of embodiments of the probe. Further alternative aspects may include discontinuities in the tubes to allow coolant to reach the interior surface of the probe more directly but, in certain examples, vary the degree and amount of flow by various holes, discontinuities, sizes of tubes, diameters, and amount of return tubes. Alternative embodiments of certain elements may include solid interior probes or probes with interiors filled with conductive or nonconductive materials and, in some embodiments, discontinuous coils allowing direct contact by the coolant with the inner surface of the probe between the filler material and covering surface material, varying the hollow configurations of the probe that are filled with coolant. Additional variations for certain elements may include inner barriers to form controlled containers for coolant filled by tubes that take up some portion of the interior of the probe closest to the outside surface.

Various aspects and embodiments of the present invention, as described in more detail and by example below, address some of the shortfalls of the background technology and emerging needs in the relevant industries.

BRIEF DESCRIPTION OF THE DRAWINGS

The accompanying drawings, which are included to provide a further understanding of the invention and are incorporated in and constitute a part of this specification, illustrate exemplary embodiments of the invention that together with the description serve to explain the principles of the invention. In the drawings:

FIGS. 5a-5c are a side, perspective and cut-away view of an alternate embodiment of a cryogenic injection probe;

FIGS. 8a-8c are perspective and cut-away views of an alternate embodiment of a cryogenic injection probe;

FIGS. 9a-9c are perspective and cut-away views of an alternate embodiment of a cryogenic injection probe;

FIGS. 10a-10c are perspective and cut-away views of an alternate embodiment of a cryogenic injection probe;

DETAILED DESCRIPTION

Figure 1:
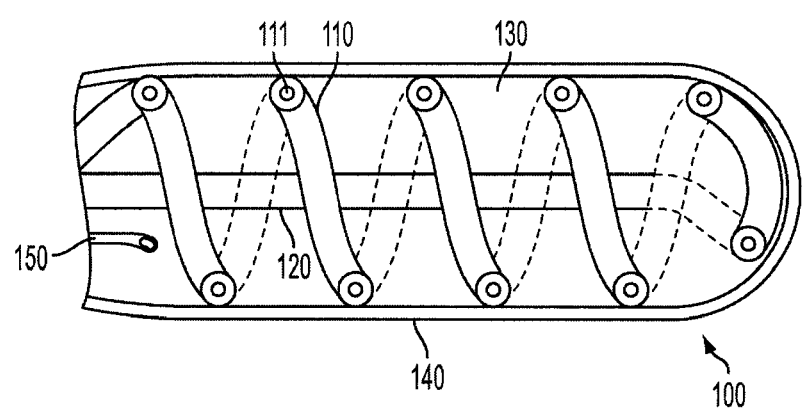
FIG. 1 is a cut-away view of an embodiment of a cryogenic injection probe.

The present invention will now be described more fully with reference to the accompanying drawings, in which preferred embodiments of the invention are shown. The invention may, however, be embodied in many different forms and should not be construed as being limited to the embodiments set forth herein. Rather, the embodiments are provided so that this disclosure will be thorough and complete, and will fully convey the concept of the invention to those skilled in the art.

It is to be understood that the present invention is not limited to the particular methodology, compounds, materials, manufacturing techniques, uses, and applications described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures.

All patents and other publications identified are incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason.

Broadly described, the present invention improves the safety of the use of a cryogenic probe through the use, for example, of double-wall containment of liquid gas refrigerant while maximizing thermal conductivity with, for example, insulating cores and increased contact surfaces. Particular aspects of the present invention may also improve the monitoring of a refrigerant leak within the probe by placing, for example, a transducer in the region between the injection coil and outer jacket. The present invention may also enlarge or increase the thermally transmittive area at the distal end of the catheter or probe (the tip region). The liquid gas refrigerant or cryogen may stay in liquid form from entry into the tip region until exit from the tip area while the flow is continuous and controlled, in a predictable (designed) path in the cooling zone of the catheter or probe. Multiple design features illustrated can be combined. Certain examples of the contemplated improvements are described in more detail below.

In one embodiment, as shown in FIG. 1, the cryogenic probe 100 has an inner injection coil 110 which may be made of, for example, a formed tube containing a narrow bore 111 for which the refrigerant may pass through. After the refrigerant travels through the inner injection coil 110, it exits the probe though the return line 120. The capillary tube is preferably made of the shape memory alloy Nitinol (NiTi) but other materials may be used containing the preferred properties of high thermal conductivity and flexibility. It is, for example in certain embodiments preferred that the capillary tube be continuous to eliminate any connecting points that are generally the most common leak points.

Alternative embodiments, however, may more preferably contain discontinuous tubes as, for example, depicted in other embodiments below to increase the transfer of coolant more directly to the probe material closest to the tissue and potentially further enlarge the contact area between the cooling component and the tissue. This discontinuity may, for example, improve heat transfer to the tissue.

An outer jacket 140 encloses the coil 110 and forms the probe chamber 130. The outer jacket is made of a thermally conductive material. In a preferred embodiment, the inner coil 110 is in contact with the outer jacket 140 to maximize the heat transfer capability of the probe. The outer jacket is in certain embodiments preferably polyurethane but can be any product thermally transmissive and also preferably flexible and perhaps multilayered.

A transducer 150 may be located within the probe chamber 130 and may monitor pressure or temperature or both for sudden changes in parameters, indicating a leak in the capillary tube. The transducer may be, for example MEMS or fiber optic, but can also be any other suitable pressure or temperature or combined transducer.

Figure 2:
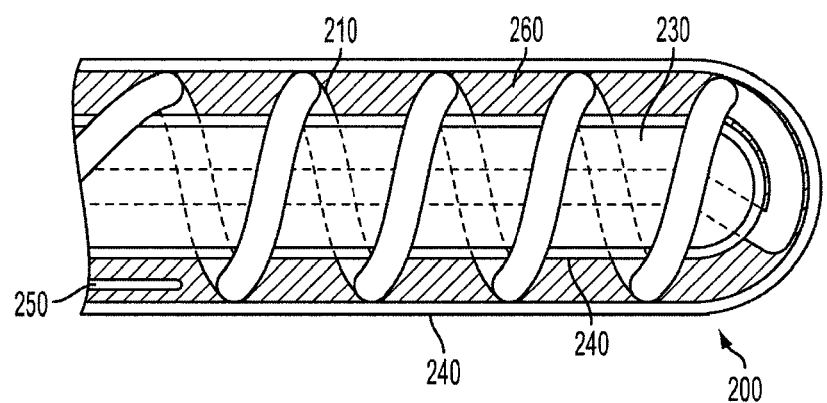
FIG. 2 is a cut-away view of an alternate embodiment of a cryogenic injection probe.

In another embodiment, as shown in FIG. 2, the cryogenic probe 200 has the inner injection coil 210 located within an inner jacket 260 and both are encapsulated by outer jackets 240. The inner jacket 260 is preferably designed or made of a material to transmit pressure and temperature variations so that the transducer 250 that is also located within the inner jacket 260 may monitor the temperature or pressure or both within the inner jacket. The probe chamber 230 may be filled with an insulating or thermally reflective material to maximize the thermal transmission between the inner injection coil 210 and the outer portion of the outer jacket 240.

Figure 3:
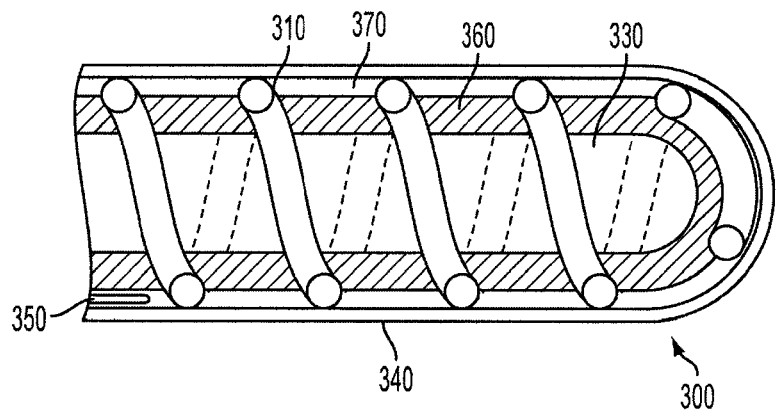
FIG. 3 is a cut-away view of an alternate embodiment of a cryogenic injection probe.

In yet another embodiment, as shown in FIG. 3, the cryogenic probe 300 has the inner injection coil 310 partially embedded into an inner jacket 360. The inner jacket 360 forms a probe chamber 330. An outer jacket 340 encloses the coil 310 and forms a jacket chamber 370. A transducer 350 is located within the jacket chamber 370 and may monitor pressure or temperature or both for sudden changes in parameters, indicating a leak in the capillary tube.

The inner jacket 360 is made of an insulating or a thermally reflective material so that the thermal transmission between the inner injection coil 310 and the outer jacket 340 is maximized.

Figure 4:
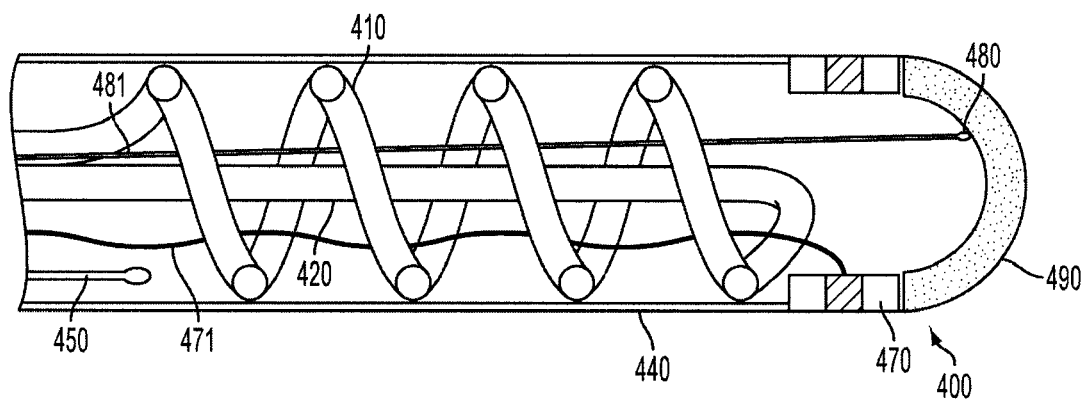
FIG. 4 is a cut-away view of an alternate embodiment of a cryogenic injection probe.

In yet another embodiment, as shown in FIG. 4, the probe 400 contains a sensor 470 adjacent to the inner injection coil 410 which may be, for example, one or multiple ECG sensor (s). Probe 400 also includes a probe tip 490. One or multiple pull wire(s) 481 is connected to probe tip 490 at connection point 480. The operator of the probe 400 may be able to change the shape of the probe 400 through the pushing and pulling of the pull wire 481. Both the sensor wire 471 and the pull wire 481 run along with the return line 420 through the middle portion of the probe 400. An outer jacket 440 encloses the coil 410 and transducer 450 is located within the probe and may monitor pressure or temperature or both.

FIGS. 5a-5c depict a further embodiment wherein a single injection tube 510 may be shaped in a longitudinal manner to increase the mass of the cryogen at the distal section of the probe. The distal section may have a length, for example, between 15 mm and 50 mm and/or may be encapsulated with a metal tip or thin polymeric sleeve 540. The space between the injection tube 510 and the sleeve 540 may be filled or packed with conductive filler materials, including, for example, conductive foam, conductive gel, steel or copper wool. In an alternate embodiment, not shown, the injection tube may be coated with a conductive material to increase thermal conductivity.

Figure 6A:
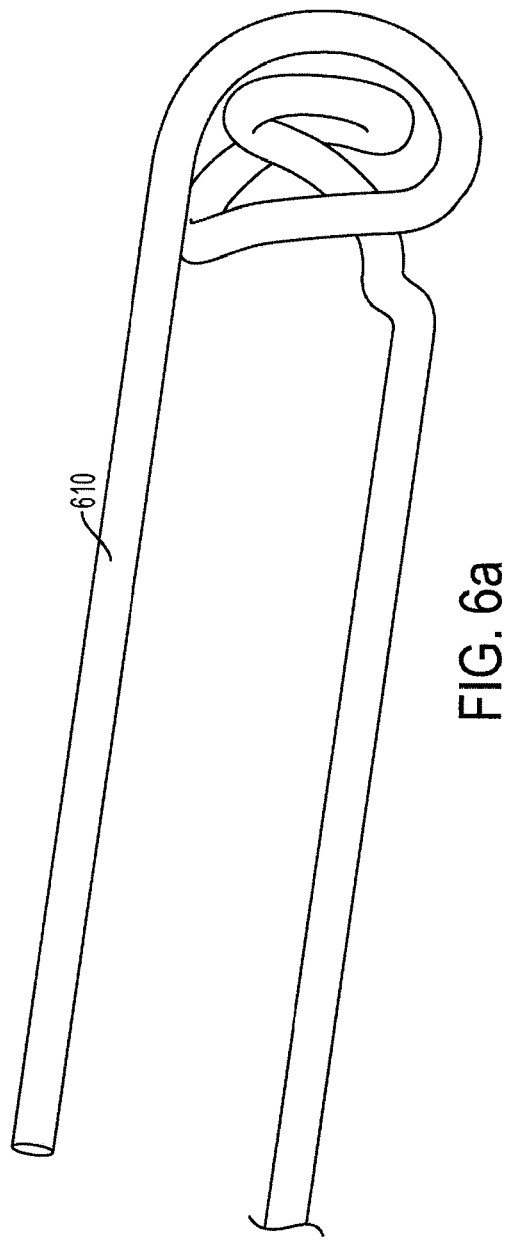
FIGS. 6a-6b are a perspective and close up view of an alternate embodiment of the injection tube of the present invention.
Figure 6B:
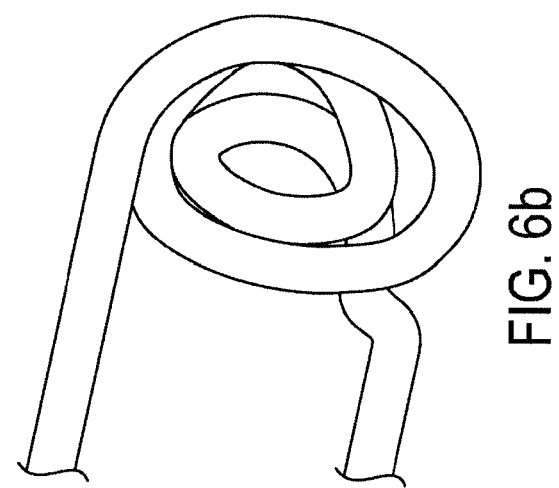

In another embodiment, as shown in FIGS. 6a-6b, a single injection tube 610 may be shaped in a spherical form at the distal end (9F-15F). This spherical form may produce an ice ball as the cryogen flows through the single injection tube 610. The tip of the probe may be encapsulated or, alternatively, the catheter or probe may be designed with the spherical section of the tube protruding from the shaft, thus allowing the injection tube to contact tissue directly.

Figure 7:
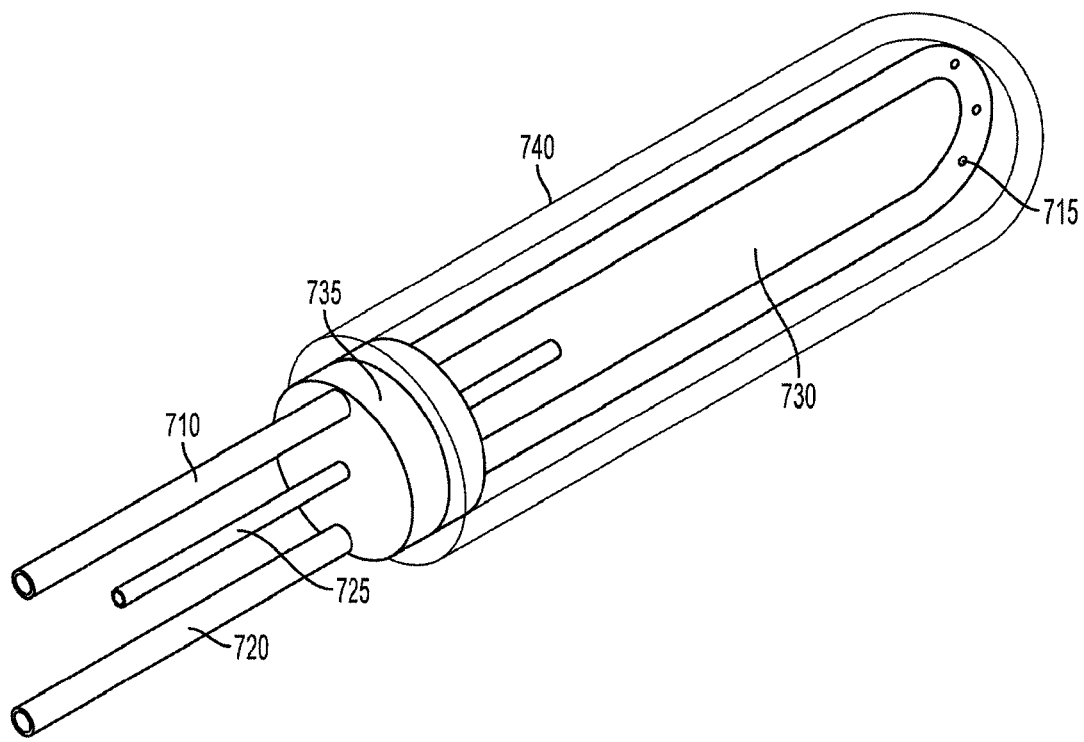
FIG. 7 is a perspective view of an alternate embodiment of a cryogenic injection probe.

A further embodiment, shown in FIG. 7, may comprise a single injection tube 710 which enters the metal tip 740 and then loops back out of the tip 740 through an exit tube 720. In one exemplary embodiment it may be contemplated to include from, for example, one to twenty micro holes 715 that may be drilled, via laser or other method known in the art, into the single injection tube 710 to allow some cryogen to strategically flow onto the inner surface of the tip 740, providing a localized "cooling boost." A plug 735 may, for example, be provided to seal the proximal end of the probe chamber 730 formed by the metal tip 740. The amount of cryogen flowing out of the micro holes 715 may, for example, be controlled by adjusting injection pressure and backpressure applied to the small tube 725 that returns leaked cryogen. The cryogen may, in certain embodiments, remain in liquid form.

In yet another embodiment, shown in FIGS. 8a-8c, the liquid cryogen may, for example, flow through the injection tube 810 to the distal end of the tip. The injection tube 810 may, for example, bring to and release cryogen to the proximal portion of the tip by various alternative embodiments. An outer jacket or sleeve 840 encapsulates the injection tube 810. The cryogen may be released from the injection tube 810 at the distal tip and then spiral back through a grooved fitting 811 to be collected by an exit tube 820. Cryogen may, for example, spiral on the grooves to the distal end of the tip and then may further spiral back through a different return groove such as the depicted helical groove. The spiral movement keeps a flow of liquid cryogen at the inside surface of the tip at all times. The grooved fitting may, for example, preferably be of highly conductive metal although for certain embodiments an insulating material may be desired. A fitting may, for example consist of two helical grooves concentrically aligned and connected at the distal end.

Figure 9A:
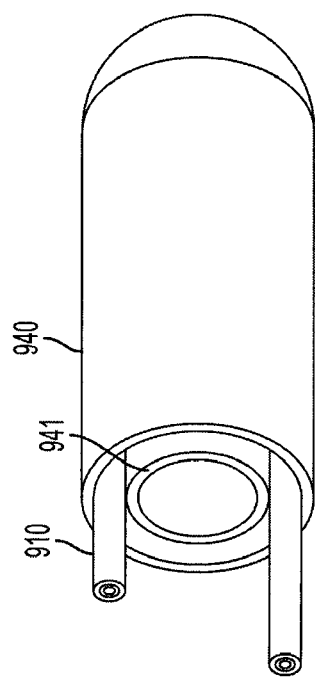
Figure 9B:
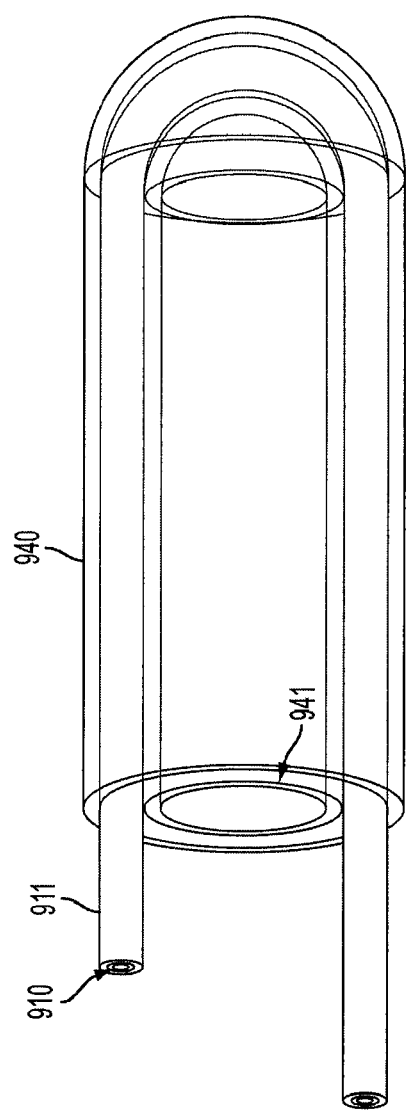

In a further embodiment, shown in FIGS. 9a-9c, the single injection tube 910 which may, or may not, be discontinuous or perforated, may be encapsulated by a metal cap or polymeric sleeve 940. The liquid cryogen may flow through the injection tube 910. An inner cap or sleeve 941 inside the metal cap or polymeric sleeve 940 may, for example, be positioned inside the single injection tube 910. FIG. 9c shows an embodiment which may improve thermal transmissivity by packing the space between the inner cap 941 and outer cap 940 with conductive filler materials 942, such as, for example, conductive foam, conductive gel, steel or copper wool. FIGS. 9b and 9c depict an embodiment wherein the single injection tube 910 is coated with a conductive coating or sleeve 911, to increase thermal conductivity. In FIGS. 10a-10c, the injection tube may, for example, be double wound 1010 between the inner cap 1041 and outer cap 1040.

Figure 11A:
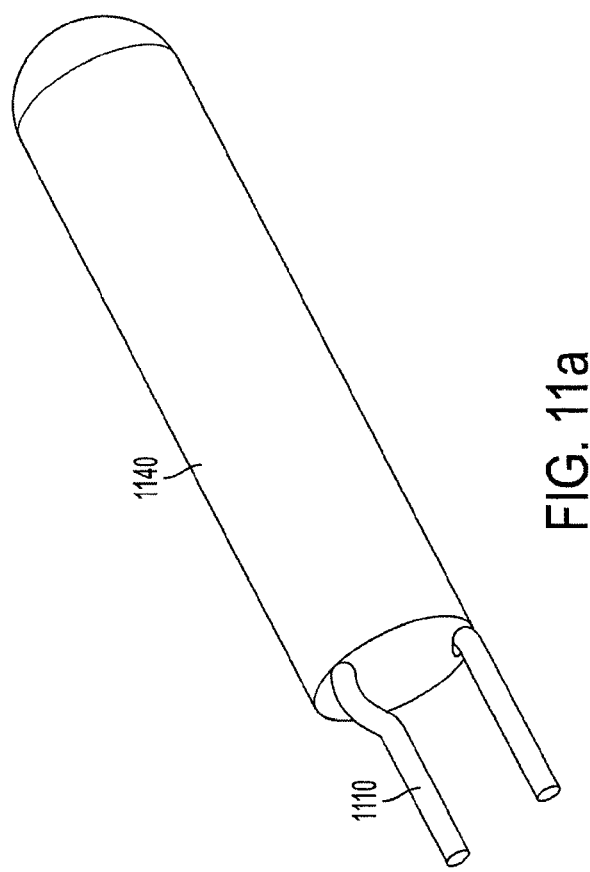
FIGS. 11a-11b are perspective and cut-away views of an alternate embodiment of a cryogenic injection probe.
Figure 11B:
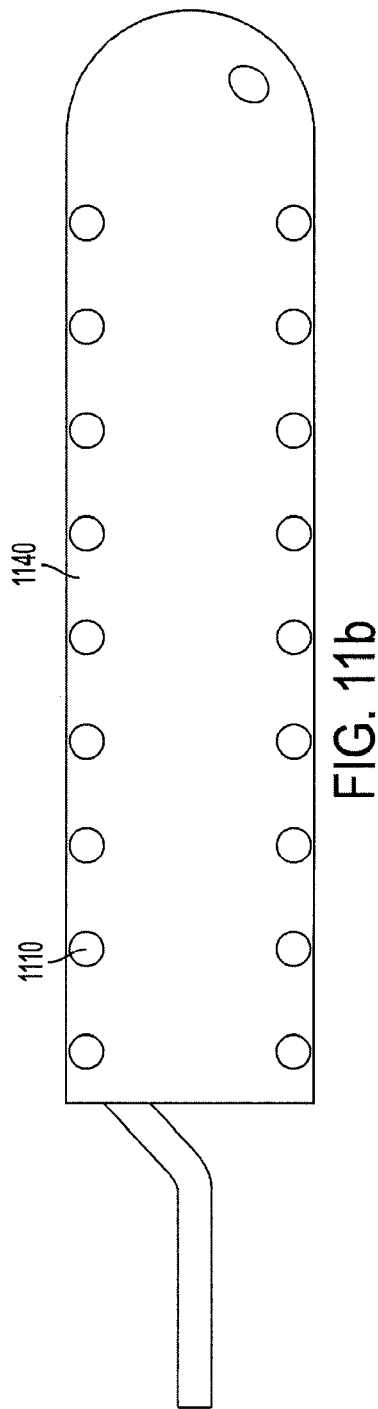

In yet a further embodiment, shown in FIGS. 11a-11b, a double wound injection tube 1110 may, for example, be insert molded into a solid metal tip 1140. This embodiment may maximize thermal conductivity by having fewer or no spaces, and thus less or no convection. The tip molding material may, for example, be a highly conductive metal such as silver, copper or gold.

Figure 12A:
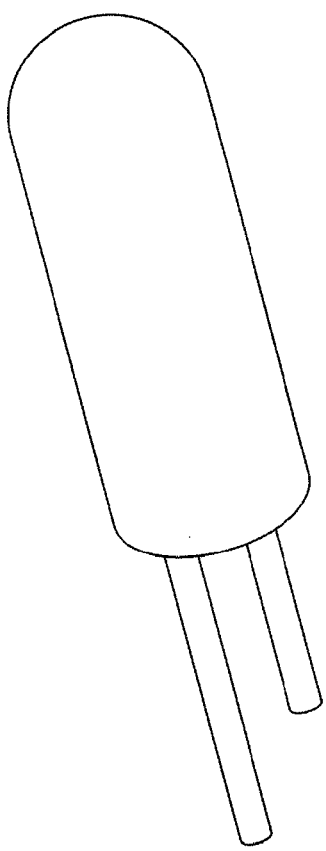
FIGS. 12a-12b are perspective and cut-away views of an alternate embodiment of a cryogenic injection probe.
Figure 12B:
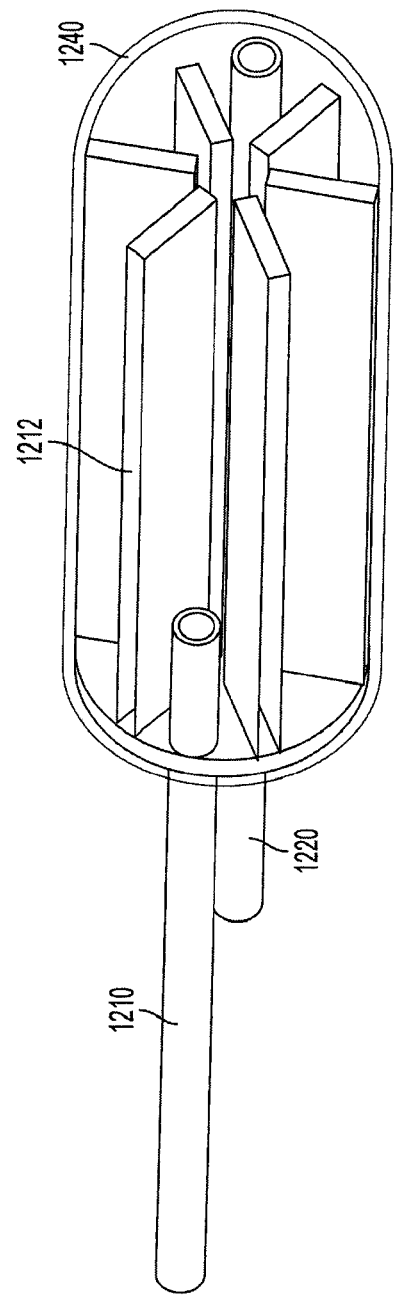

In a further embodiment, shown in FIGS. 12a-12b, an injection tube 1210 may be configured to enter a closed tip 1240 and disperse, for example, liquid cryogen. Fins 1212 within the tip 1240 may be configured to distribute the cryogen, causing increased heat transfer. The liquid cryogen may exit the tip 1240 through the return line 1220.

Figure 13A:
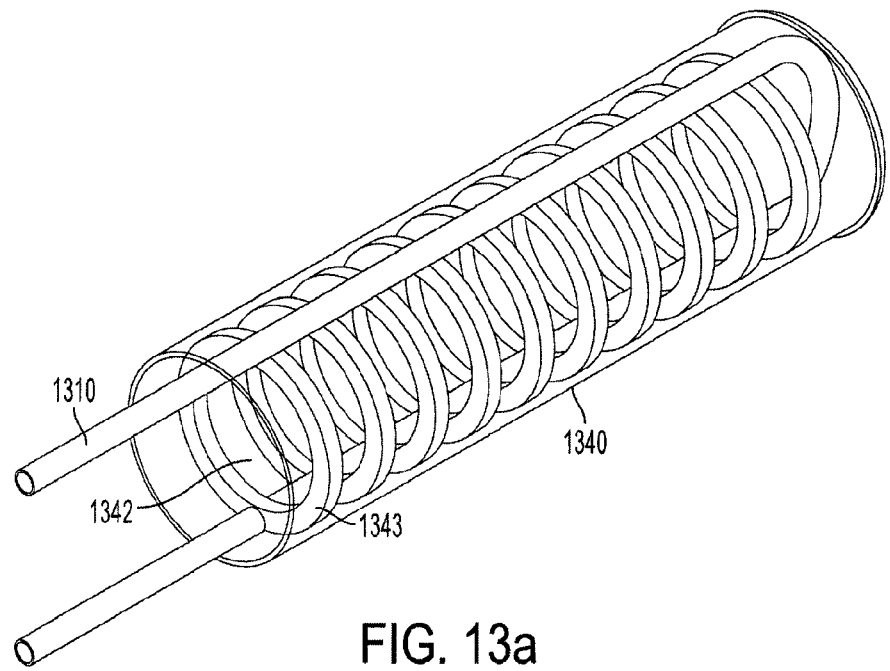
FIGS. 13a-13d are perspective and cut-away views of an alternate embodiment of a cryogenic injection probe.
Figure 13B:
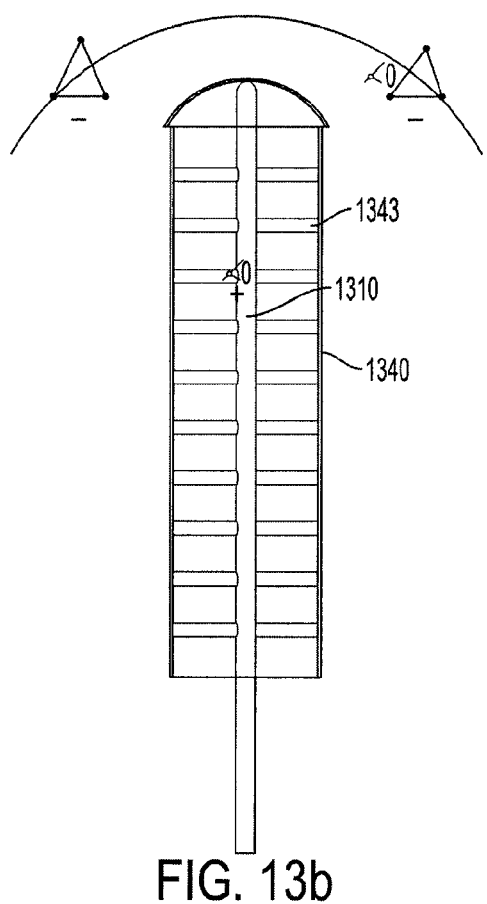
Figure 13D:
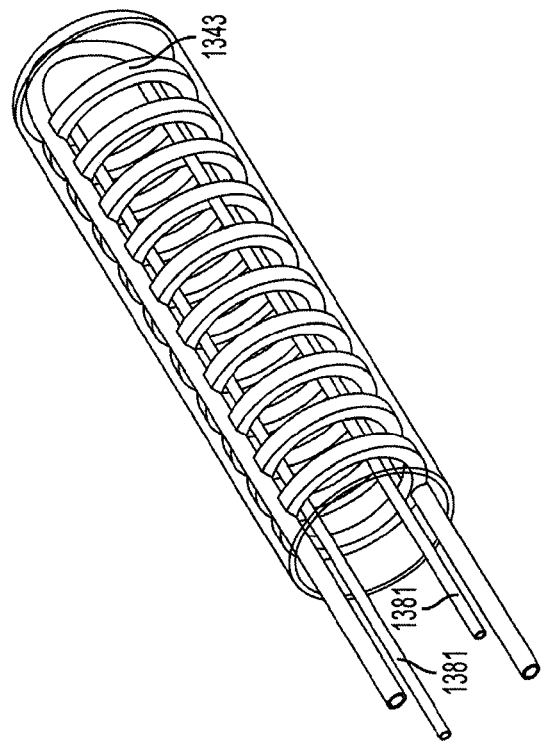
Figure 13C:
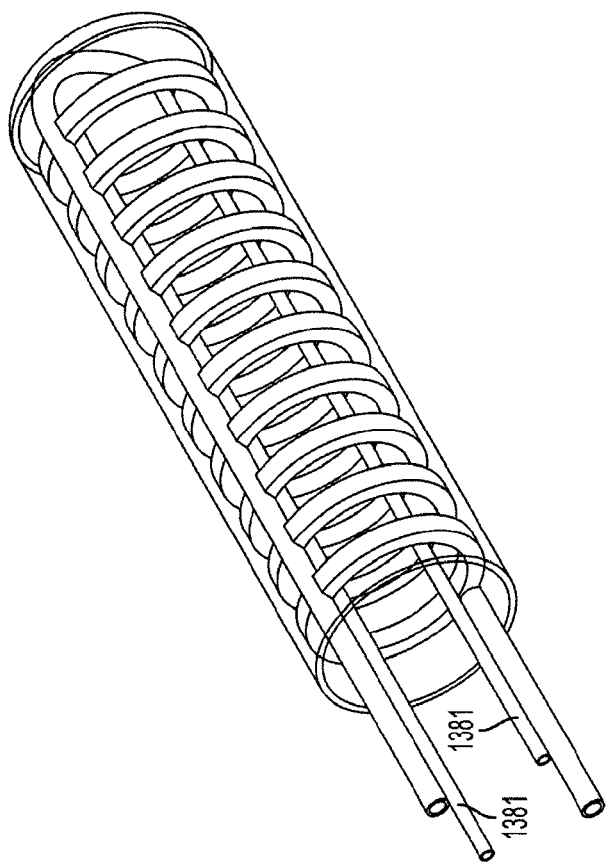

In yet a further embodiment, shown in FIGS. 13a-13d, a single continuous, or alternatively discontinuous or perforated, injection tube 1310 may loop at least once at the distal end of a tip encased in a thin polymer sleeve 1340. One or more metal support rings 1343 may be provided to create a flexible cylindrical cooling structure. These rings may also serve as conducting fins to increase the heat flow from the surface of the sleeve 1340. The injection tube 1300 may then flex in one plane, as shown in FIG. 13b. The cooling segment may also able to conform to tissue. As shown in FIGS. 13c-13d, one or more pull wires 1381 may be added to make the cooling segment deflectable. The pull wires 1381 may pass alongside the rings 1343 or through holes in the rings 1343 and be anchored to the most distal ring.

Figure 14B:
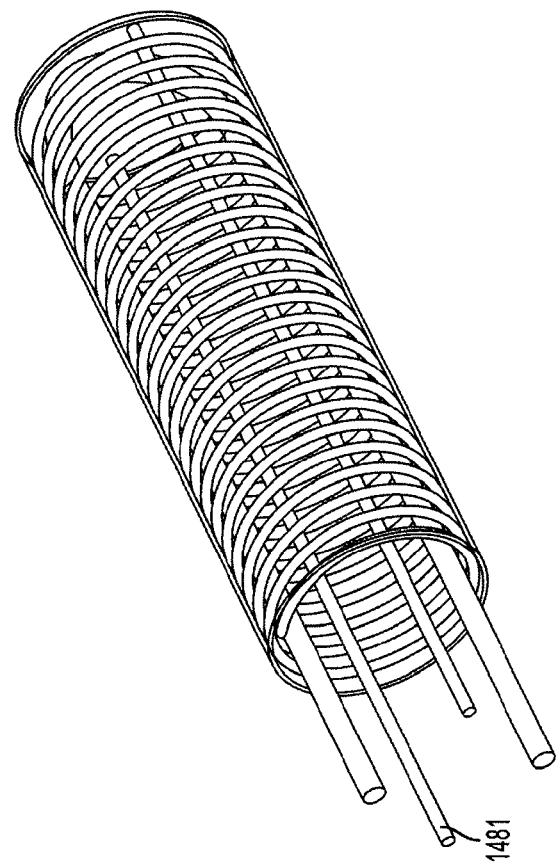
FIGS. 14a-14b are perspective views of an alternate embodiment of a cryogenic injection probe.
Figure 14A:
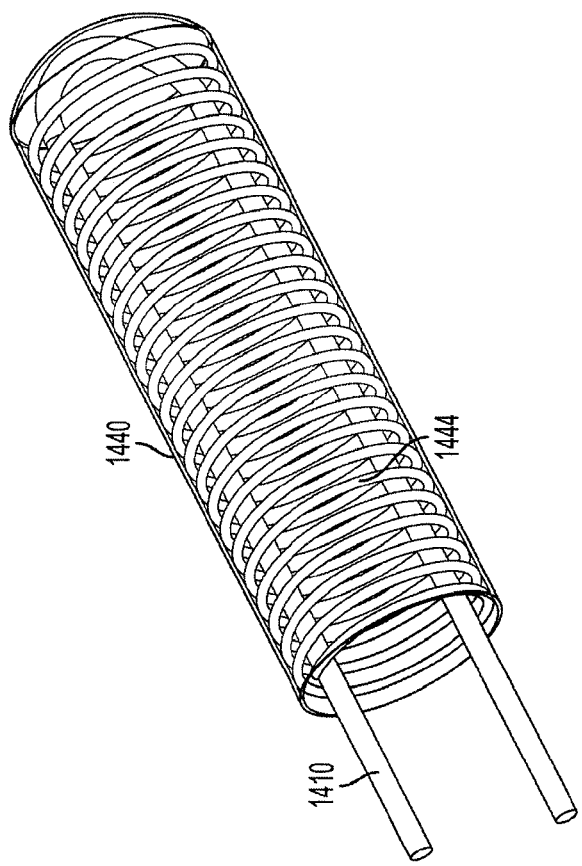

FIG. 14a depicts an embodiment of the present invention wherein a metal spring 1444 provides a flexible cylindrical cooling structure for a single continuous injection tube 1410 to pass through. Pull wires 1481 may also be incorporated and anchored at the distal end of the tip 1440.

Figure 15A:
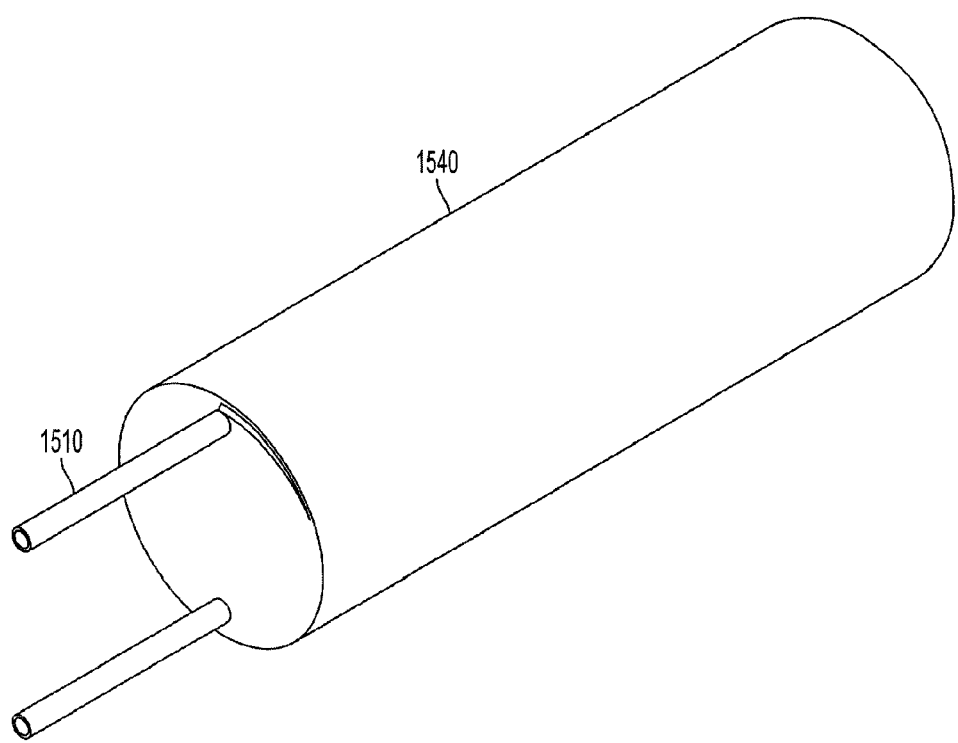
FIGS. 15a-15c are perspective views of alternate embodiments of a cryogenic injection probe.
Figure 15B:
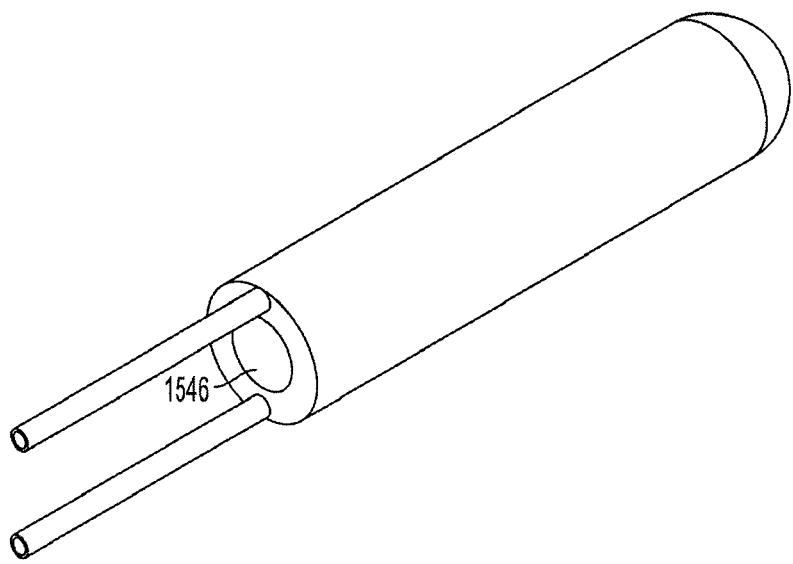
Figure 15C:
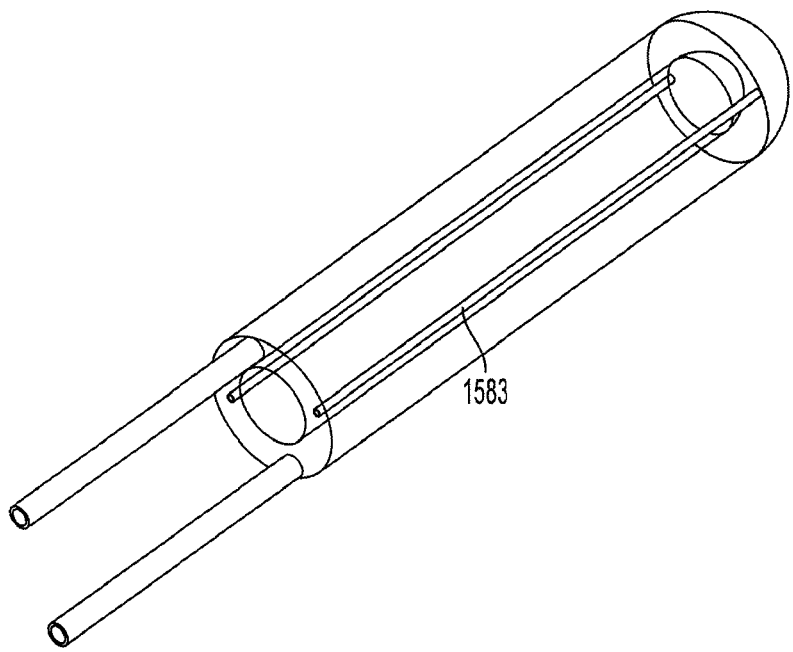

In yet a further embodiment of the invention, shown in FIGS. 15a-15c, a solid tip 1540 may be molded over the injection tube 1510. The tip 1540 may be a highly conductive polymer which exhibits flexible characteristics and may conform to tissue. It may also be able to elastically bend when compressed. Newly engineered polymers are available, such as, for example, CoolPoly® E-series thermal conductive polymer, which has thermal conductivity up to K=100 W/mK. In comparison, stainless steel has K=20 W/mK. The highly thermal conductive polymer can, for example, be combined with other known polymers to formulate the desired flexibility. FIG. 15b depicts a flexible thermal conductive polymer tip 1540 overmolded onto the injection tube 1510 with an inner cavity 1546. This inner cavity 1546 may provide space for deflecting wires or deflection mechanisms consisting of one or more shims. FIG. 15c shows a flexible thermal conductive polymer tip 1540 overmolded with holes or channels 1583 for the placement of pull wires. The pull wires may be anchored to a metal fitting at the distal end of the tip 1540.

Figure 16C:
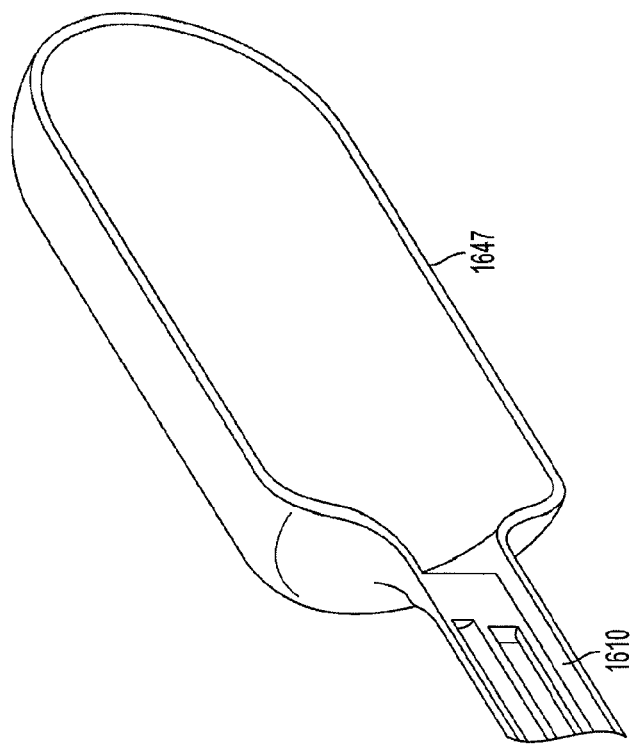
FIGS. 16a-16c are a side, perspective and cut-away views of an alternate embodiment of a cryogenic injection probe.
Figure 16A:
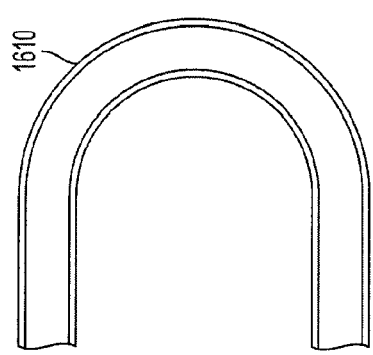
Figure 16B:
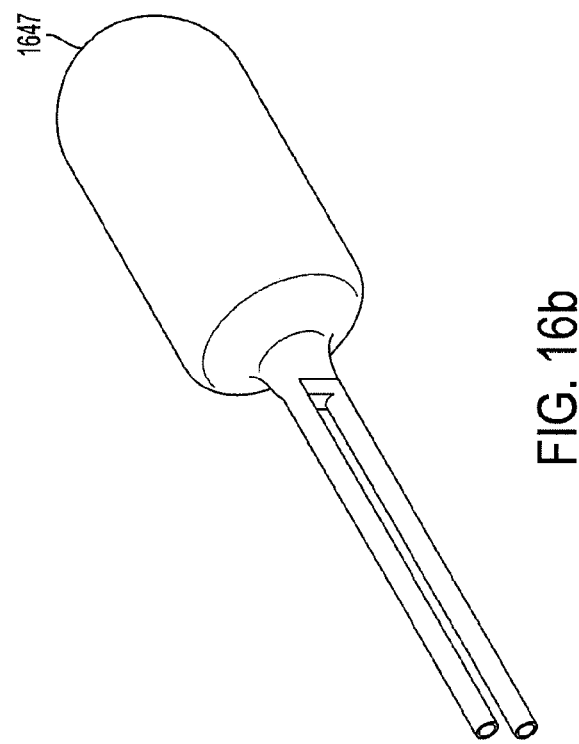

In yet a further embodiment, shown in FIGS. 16a-16c, the single component, continuous injection tube 1610 may be flared at the inner and outer diameters to create a bulb 1647 at the distal cooling section. This bulb 1647 may increase the volume capacity of liquid Nitrogen and thus increase the cooling capacity at this section of the cryogenic probe.

Figure 17A:
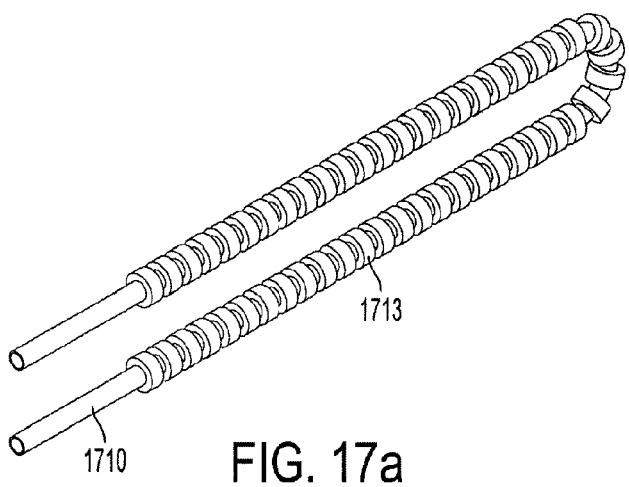
FIGS. 17a-17g are perspective and cut-away views of an alternate embodiment of a cryogenic injection probe.
Figure 17B:
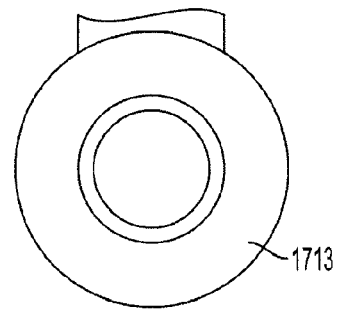
Figure 17C:
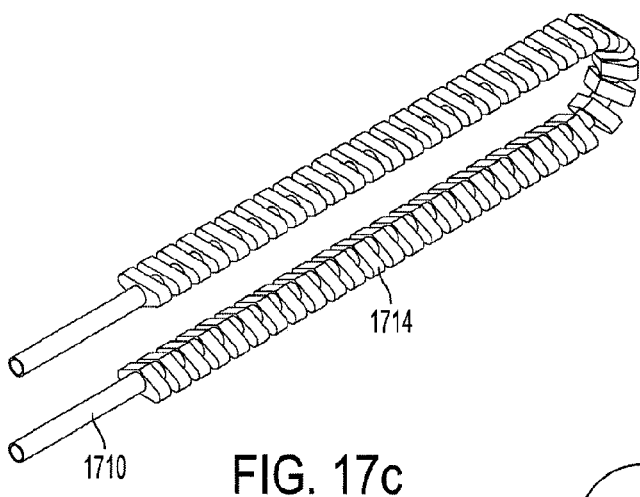
Figure 17D:
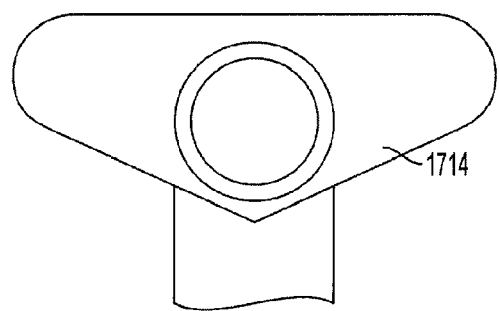
Figure 17E:
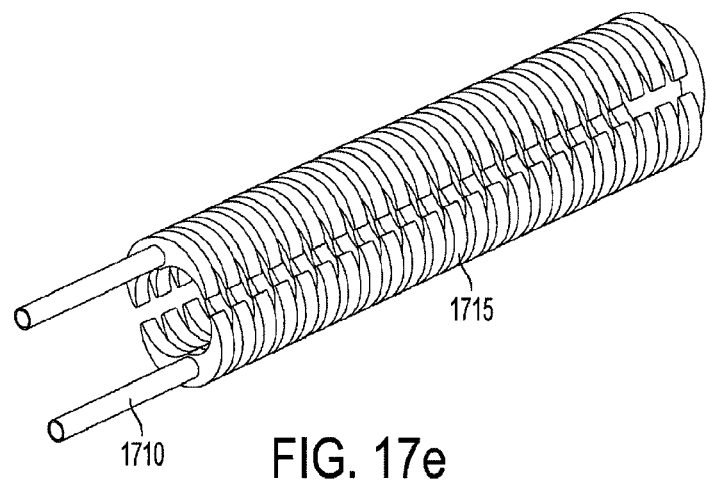
Figure 17F:
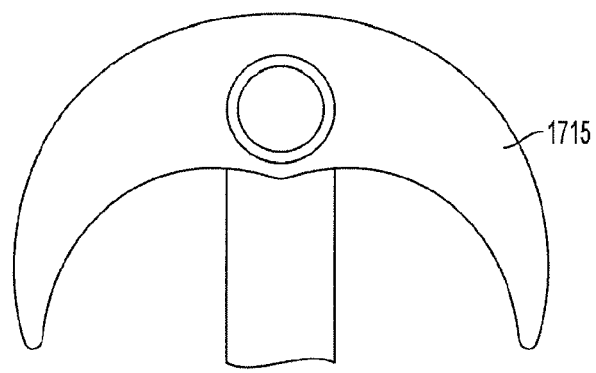
Figure 17G:
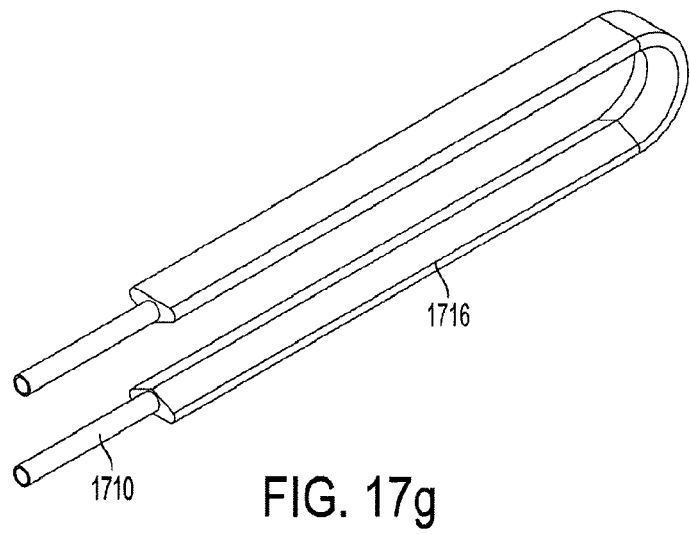

In an embodiment, shown in FIGS. 17a-17g, the exemplary single component, continuous injection tube 1710 may be surrounded by one or more fittings to, for example, increase the thermal transmissive region. These fittings may be placed with constant or variable spacing to provide desired flexibility and heat transfer capability. The fittings may be made of, for example, metal or thermal conductive polymer. In FIGS. 17a-17b, the fitting 1713 is, for example, provided as a donut shaped ring surrounding the injection tube 1710. In a further embodiment, FIGS. 17c-17d, the thermal conductive fitting may be a curved, triangular shape 1714, which provides for increased contact area with the outer wall of a sleeve or cap (not shown), thus allowing more heat absorption from or transfer to the tissue. FIGS. 17e-17f show another fitting 1715 comprising one or more crescent shapes, providing more surface area contact with the inner wall of a sleeve or cap. This embodiment may also provide a cylindrical structure to the tip area, thereby supporting a flexible sleeve. In a further embodiment, a thermal conductive sleeve 1716, may replace the interspaced fittings on the injection tube 1710. The sleeve may be a flexible thermal conductive material and may be provided as a unitary body or in segments.

It should be noted that the continuous single loop injection tube as shown, for example, in FIGS. 13a-15c, may be looped more than once longitudinally. For example, FIG. 5a depicts an injection tube looped five times. Depending on the size of the injection tube and the cooling segment length, the cooling segment may retain some flexibility even with multiple looping.

Further, it should be appreciated that the various embodiments of tubes, although depicted as cylindrical, may be provided in any shape capable of providing a passageway, including but not limited to oval, rectangular, expanded in portions, punctured or with windows or apertures. These tubes may also be configured, for example, like a bendable straw with an accordion portion to increase flexibility and heat transfer capability or adjust proximity to an outer sheath or tissue. Any of these tubes may be provided with various configurations of encapsulation or enshrouding to adjust transmissive properties and/or flexibility of the probe assembly.

Although the embodiments as in the figures discussed above depict, as examples, that there may be substantial space between each subsequent winding, this depiction is only for the purposes of schematically showing each of the components of the cryogenic probe. It is preferred in certain embodiments, that the windings of the coil be placed as closely as possible so as to maximize thermal conductivity but with some space to allow for probe flexibility. Additionally, the length of the portion of the inner injection coil may, for example, vary depending on the application.

In certain of these embodiments, the transducer may, for example, preferably be monitoring the pressure in the region between the injection coil and the outer jacket. Because of the outer jacket, a leak in the injection coil may not result in gas entering into the bloodstream. Additionally, the transducer may, for example, preferably detect the change in pressure or temperature or both of the area, for example, enclosed by the outer jacket. System monitoring equipment may then quickly shut down the system before the internal leak has any chance of spreading.

The embodiments described above are exemplary only. One skilled in the art may recognize variations from the embodiments specifically described here, which are intended to be within the scope of this disclosure. As such, the invention is limited only by the following claims. Thus, it is intended that the present invention cover the modifications of this invention provided they come within the scope of the appended claims and their equivalents. Further, specific explanations or theories regarding the formation or performance of electrochemical devices according to the present invention are presented for explanation only and are not to be considered limiting with respect to the scope of the present disclosure or the claims.

What is claimed is:

1. A cryogenic probe comprising:
an elongated tube comprising an injection tube, a coil and a return tube, wherein the coil comprises a first end a second end, said first end in fluid communication with said injection tube, and said second end in fluid communication with and directly and mechanically coupled to a distal end of said return tube;
   an outer jacket enclosing said coil, said outer jacket having an inner surface and an outer surface;
   an inner jacket comprising a proximal end and a distal end disposed within said outer jacket and forming a probe chamber, wherein said distal end of said inner jacket is disposed entirely within said outer jacket and wherein said distal end of said inner jacket is sealed, said inner jacket having an inner surface and an outer surface, wherein a space exists between the outer surface of said inner jacket and the inner surface of said outer jacket forming a jacket chamber; and
   a tip at the distal portion of the probe.

2. The cryogenic probe of claim 1 wherein said probe chamber is, at least in part, hollow.

3. The cryogenic probe of claim 1 wherein said coil is located at least in part in a position that presses against said outer jacket.

4. The cryogenic probe of claim 1 further comprising a thermally transmissive material positioned between at least a portion of said coil and at least a portion of said outer jacket.

5. The cryogenic probe of claim 1, wherein said coil is at least in part helical.

6. The cryogenic probe of claim 1, wherein said coil is at least in part in the form of at least one loop.

7. The cryogenic probe of claim 6, wherein said coil is more densely looped near the tip of the probe.

8. The cryogenic probe of claim 1, wherein said coil further comprises an encapsulation membrane.

9. The cryogenic probe of claim 8, wherein said encapsulation membrane is thermally transmissive.

10. The cryogenic probe of claim 1, wherein said injection tube, said return tube, and said coil each comprises an inner tube diameter and said coil inner tube diameter is smaller than said injection tube and said return tube inner tube diameters.

11. The cryogenic probe of claim 10, wherein said coil inner tube diameter is smaller at the tip of the probe.

12. The cryogenic probe of claim 1, wherein said injection tube, said return tube, and said coil each comprises an inner tube diameter and said coil inner tube diameter is larger than said injection tube and said return tube inner tube diameters.

13. The cryogenic probe of claim 1, further comprising a transducer.

14. The cryogenic probe of claim 13, wherein said transducer monitors pressure parameters of said probe chamber and detects a leak from said coil.

15. The cryogenic probe of claim 13, wherein said outer jacket is impermeable.

16. The cryogenic probe of claim 15, wherein said transducer is placed within said probe chamber.

17. The cryogenic probe of claim 16, wherein said inner jacket comprises a material capable of transmitting pressure variations.

18. The cryogenic probe of claim 17, wherein said transducer monitors pressure parameters of said probe chamber.

19. The cryogenic probe of claim 16, wherein said inner jacket comprises a material capable of transmitting temperature variations.

20. The cryogenic probe of claim 19, wherein said transducer monitors temperature within said probe chamber.

21. The cryogenic probe of claim 15, wherein said transducer is placed within said jacket chamber.

22. The cryogenic probe of claim 21, wherein said transducer monitors pressure parameters of said jacket chamber.

23. The cryogenic probe of claim 21, wherein said transducer monitors temperature within said jacket chamber.

24. The cryogenic probe of claim 1, wherein a refrigerant is passed through said coil.

25. The cryogenic probe of claim 24, wherein said refrigerant is a liquefied gas.

26. The cryogenic probe of claim 1, wherein said coil is in thermal communication with said outer jacket.

27. The cryogenic probe of claim 1, wherein the material of said coil comprises Nitinol.

28. The cryogenic probe of claim 1, wherein said coil is disposed within said jacket chamber.

29. The cryogenic probe of claim 1, wherein said coil is partially disposed within said jacket chamber.

30. The cryogenic probe of claim 1, wherein the outer jacket is a metal.

31. The cryogenic probe of claim 1, wherein the outer jacket has a bellows shape.

* * * * *